United States Patent

Kazmaier et al.

[11] Patent Number: 5,817,824
[45] Date of Patent: Oct. 6, 1998

[54] PROCESSES FOR STABEL FREE RADICALS

[75] Inventors: Peter M. Kazmaier, Mississauga; Marko D. Saban, Etobicoke; Karen A. Moffat, Brantford; Michael K. Georges, Guelph, all of Canada

[73] Assignee: Xerox Corporation, Stamford, Conn.

[21] Appl. No.: 905,266

[22] Filed: Aug. 1, 1997

[51] Int. Cl.6 .................................................. C07D 211/94
[52] U.S. Cl. ............................................................. 546/242
[58] Field of Search ................................................ 546/242

[56] References Cited

U.S. PATENT DOCUMENTS

| | | | |
|---|---|---|---|
| 3,534,048 | 10/1970 | Murayama | 260/293 |
| 4,581,429 | 4/1986 | Solomon et al. | 526/220 |
| 5,059,657 | 10/1991 | Druliner et al. | 525/244 |
| 5,322,912 | 6/1994 | Georges et al. | 526/204 |
| 5,401,804 | 3/1995 | Georges et al. | 525/267 |
| 5,412,047 | 5/1995 | Georges et al. | 526/204 |
| 5,455,315 | 10/1995 | Paine et al. | 526/79 |
| 5,498,679 | 3/1996 | Moffat et al. | 526/204 |
| 5,530,079 | 6/1996 | Veregin et al. | 526/219.3 |
| 5,545,504 | 8/1996 | Keoshkerian et al. | 430/137 |
| 5,549,998 | 8/1996 | Georges et al. | 430/109 |
| 5,552,502 | 9/1996 | Odell et al. | 526/234 |

Primary Examiner—Alan L. Rotman
Assistant Examiner—Charanjit S. Awlakh
Attorney, Agent, or Firm—E. O. Palazzo

[57] ABSTRACT

A process for the preparation of 4-oxo-2,2,6,6-tetramethyl-1-piperidinyloxy which comprises the reaction of triacetone amine in the presence of a catalyst and a peroxide.

23 Claims, No Drawings

5,817,824

1

PROCESSES FOR STABEL FREE RADICALS

PENDING APPLICATIONS AND PATENTS

Illustrated in U.S. Pat. No. 5,412,047, the disclosure of which is totally incorporated herein by reference, is a polymerization process for the preparation of homopolymeric acrylates containing thermoplastic resin or resins comprising heating a mixture comprised of a free radical initiator, an oxo nitroxide stable free radical agent, at least one polymerizable acrylate monomer compound, and optionally a solvent to form a homopolymeric acrylate containing thermoplastic resin or resins with a high monomer to polymer conversion and a narrow polydispersity. Illustrated in copending application U.S. Ser. No. 348,021, the disclosure of which is totally incorporated herein by reference, is a free radical polymerization process for the preparation of thermoplastic resin comprising heating a mixture of a free radical initiator, a stable free radical agent, and at least one polymerizable monomer compound, and wherein said heating is accomplished at a temperature of from about 40° to about 100° C. in the presence of ultrasonic irradiation; cooling said mixture; and optionally isolating said thermoplastic resin, and washing and drying said thermoplastic resin. Illustrated in U.S. Pat. No. 5,728,747 the disclosure of which is totally incorporated herein by reference, is a free radical polymerization process for the preparation of a thermoplastic resin or resins comprising heating a mixture of a free radical initiator, a stable free radical agent, and at least one polymerizable monomer compound to form said thermoplastic resin or resins with a high monomer to polymer conversion; cooling said mixture; optionally isolating said thermoplastic resin or resins; and optionally washing and drying said thermoplastic resin or resins.

Stable free radical polymerization processes are also illustrated in U.S. Pat. No. 5,401,804, U.S. Pat. No. 5,322,912, U.S. Pat. No. 5,412,047, U.S. Pat. No. 5,455,315, U.S. Pat. No. 5,545,504, U.S. Pat. No. 5,552,502, U.S. Pat. No. 5,549,998, U.S. Pat. No. 5,530,079, U.S. Pat. No. 5,498,679, U.S. Pat. No. 5,449,724, U.S. Ser. No. 08/214,518, and U.S. Ser. No. 08/223,418, the disclosures of each of which are totally incorporated herein by reference. The patents, such as the U.S. Pat. No. 5,322,912 illustrate stable free radical polymerization processes, and wherein a transition metal compound is not selected.

BACKGROUND OF THE INVENTION

The present invention relates, for example, to processes for the preparation of polymers, and more specifically, to polymerization processes and polymers thereof. In embodiments, the present invention relates, for example, to a stable free radical moderated process for generating a thermoplastic polymer resin or resins that have narrow polydispersities, that is, narrow molecular weight distributions as illustrated by the ratio $M_w:M_n$, where $M_w$ is the weight average molecular weight of the polymer, and $M_n$ is the number average molecular weight of the polymer, and easily controllable modality, from at least one monomer compound comprising heating for an effective period of time a mixture of a free radical initiator, a stable free radical agent, and at least one polymerizable monomer in the presence of a transition metal and under conditions such that all polymer chain formations are initiated at about the same time; cooling the mixture to effectively terminate the polymerization; isolating the thermoplastic resin product; and optionally washing and drying the polymer product, and wherein the stable free radical compound, especially TEMPONE, is prepared from triacetone amine and which stable free radical compound is particularly useful in stable free radical polymerization processes wherein acrylate monomers are polymerized. The polymer resins generated in embodiments are, for example, essentially monomodal, and in embodiments, by repeating the heating step, that is, the combined initiation and polymerization step, there is provided a method for obtaining mixtures of monomodal polymer resins, that are compositionally the same resin type having characteristics of both narrow polydispersity and known or selectable modality. The polymeric chain growth proceeds by a pseudoliving mechanism and can provide resins of variable molecular weights, $M_w$, from very low to very high, for example less than about 10,000 up to about 400,000, and more specifically, from about 25,000 to about 300,000 while maintaining narrow molecular weight distributions or polydispersities.

PRIOR ART

The use of stable free radicals are known as inhibitors of free radical polymerizations, see for example, G. Moad et. al., *Polymer Bulletin* 6, 589 (1982). Studies by, for example, G. Moad et. al. *J. Macromol. Sci-Chem.*, A17(1), 51(1982) have reported on the use of stable free radicals as inhibitors of free radical polymerizations performed at low temperatures, for example below 90° C., and at low monomer to polymer conversions.

In a hypothetical free radical polymerization of styrene, in which chains are continually initiated over the course of the polymerization, and where chain termination by coupling processes is also occurring, calculations as described in, for example, G. G. Odian, *Principles of Polymerization,* pages 280–281, 2nd Ed., John Wiley & Sons, 1981 have shown that the narrowest polydispersity that one can theoretically obtain is 1.5. In practice, polydispersities greater than 1.5 are actually obtained. Polydispersities of between 2.0 and 2.4 are typical for free radical homopolymerizations of styrene. In the situation with copolymer systems, polydispersities of greater than 4 are generally obtained.

The accelerated stable free radical polymerization processes of the present invention enable polydispersities of between 1.10 and 1.30 for polymers, such as polystyrene, and as low as 1.4 for various copolymers.

U.S. Pat. No. 4,581,429, discloses a free radical polymerization process which controls the growth of polymer chains to produce short chain or oligomeric homopolymers and copolymers including block and graft copolymers. The process employs an initiator having the formula (in part) =N—O—X, where X is a free radical species capable of polymerizing unsaturated monomers. The molecular weights of the polymer products obtained are generally from about 2,500 to 7,000 having polydispersities generally of about 1.4 to 1.8, at low monomer to polymer conversion. The reactions typically have low conversion rates, employ relatively low reaction temperatures of less than about 100° C., and use multiple stages.

U.S. Pat. No. 5,059,657, discloses a polymerization process for acrylic and maleimide monomers by contacting the monomers with a diazotate, cyanate or hyponitrite, and N-chlorosuccinimide, N-bromosuccinimide or a diazonium salt. The polymer produced can initiate further polymerization, including use in block copolymer formation.

The polymerization processes and thermoplastic resin products thereof can be selected for a variety of specialty applications including toner resins used for electrophotographic imaging processes, wherein monomodal or mixtures of monomodal narrow molecular weight resins or block copolymers with narrow molecular weight distribution within each block component are needed, such as in thermoplastic films and coating technologies, adhesives; rubbers, lubricants, and the like.

Preparation of TEMPONE is illustrated, for example, by E. G. Rozantsev in *Free Nitroxyl Radicals,* Plenum Press, New York, on page 213 and page 214. This process is conducted at room temperature, is not rapid, for example it consumes, for example, from about 8 to about 10 days, and yields 130 to 140 grams of TEMPONE based on 155 grams of triacetone amine starting material.

FEATURES

Examples of features of the present invention include:

A feature of the present invention is to provide processes and polymers that overcome many of the problems and disadvantages of the prior art.

Another feature of the present invention is to provide free radical polymerization reaction process which enables narrow polydispersity products of, for example, homopolymeric or copolymeric thermoplastic resin products, and wherein the stable free radical compound selected, for example nitroxide TEMPONE can be prepared in high yields, and excellent purity.

Moreover, another feature of the present invention relates to economical scaleable processes for the preparation of stable free radical agents, or compounds.

SUMMARY OF THE INVENTION

The present invention relates to, for example, the preparation of thermoplastic resins comprising heating a first mixture comprised of a free radical initiator, a stable free radical agent, and at least one polymerizable monomer compound to form a first intermediate product resin; optionally cooling the first mixture; adding to the first intermediate product resin a second mixture comprised of a free radical initiator, a stable free radical agent, and at least one polymerizable monomer compound, wherein the polymerizable monomer compound of the second mixture is the same as the polymerizable monomer compound of the first mixture, and the free radical initiator and the stable free radical agent of the second mixture are the same or different from the free radical initiator and the stable free radical agent of the first mixture to form a combined mixture; heating the combined mixture to form a third mixture comprised of a mixture of thermoplastic resins comprised of a first product resin formed from the first intermediate product resin and added the second monomer and a second product resin formed from the second monomer; cooling the third mixture; optionally isolating the mixture of thermoplastic product resins from the third mixture; and optionally washing and drying the mixture of thermoplastic resins and wherein the first product resin and the second product resin each possess a narrow polydispersity and the mixture of thermoplastic resins possesses a modality equal to 2, and wherein there is selected the nitroxide TEMPONE prepared as illustrated herein. Also, with the present invention in embodiments thereof acrylate monomers can be polymerized.

The nitroxide TEMPONE, or 4-oxo-2,2,6,6-tetramethyl-1-piperidinyloxy can be prepared by the catalytic oxidation of triacetone. More specifically, the reaction comprises heating triacetone amine in the presence of a peroxide, such as hydrogen peroxide, an aliphatic alcohol, such as methanol, and a catalyst like an alkali metal, such as sodium tungstate dihydrate. The reaction mixture is heated with stirring, followed by the extraction of the nitroxide TEMPONE with a solvent like methylene chloride, distillation of the solvent, recrystallization of the product from, for example, heptane, and thereafter filtering and drying. The reaction time is rapid, and can be, for example, from about 3 to about 7 and preferably from about 3 to about 4.5 hours. The product nitroxide TEMPONE can be identified by a number of methods, such as melting point, electron spin resonance, UV-visible spectroscopy and infrared spectroscopy. The reaction temperature is preferably, for example, from about 25° to about 45° C., the reaction time is, for example, from about 5 hours to about 24 hours, that is the reaction is rapid, and the product yields ranged, for example, from about 35 to about 80 percent.

Examples of reactants and amounts of reactants are an alkali tungstate catalyst, such as sodium, potassium, and the like, in an amount of from about 1 to about 5, or from 2 to about 4 grams; a peroxide like hydrogen peroxide, in an amount of from about 100 to about 400, or from about 200 to about 300 grams, and preferably a 30 percent hydrogen peroxide solution; a base, such as N,N,N',N'-ethylenediamine tetraacetic acid (EDTA), tetrasodium salt, N,N,N',N'-ethylenediamine tetraacetic acid tetrapotassium salt, sodium bicarbonate, potassium bicarbonate, sodium acetate, potassium acetate, sodium carbonate, potassium carbonate, and the like, in an amount of from about 5 to about 20, or from about 10 to about 15 grams; from about 250 to about 1,000, or from about 400 to about 800 grams of water; and from about 250 to about 1,000, or from about 400 to about 800 grams of an aliphatic alcohol with, for example, 1 to about 25 carbon atoms, such as methanol, ethanol, isopropanol, and the like. The reaction can be conducted in an open vessel such as a large beaker (2 liter) heated on a hot plate or in a closed vessel such as a Parr reactor.

Propagating chains are referred to as pseudoliving primarily because the stable free radical agent adds to a propagating chain and the chain is temporarily, but reversibly, terminated. As shown in the accompanying scheme, the propagating polymer chain fluctuates or is in an equilibrium condition between being temporarily terminated or suspended and being alive or living. As thermal energy is supplied from the reaction system to the bond joining the growing polymeric chain and the stable free radical agent, that is, the adduct is covalently bound to the propagating chain, for example a substituted styrene, homolytically cleaves thereby temporarily generating a living chain end radical species shown in square brackets [ ] permitting another monomer unit to insert or add to the chain and is again instantaneously, albeit short lived as determined by diffusion control, terminated or protected by the stable free radical agent as a thermally labile adduct above about 80° C. to 100° C. or latent free radical chain. Protected refers, for example, to the chain radical species being available for selective rather than indiscriminate further reaction with monomer. An unmoderated free radical polymerization chain, that is a free radical polymerization process without a stable free radical agent present in contrast has a reactive or "open" chain end throughout the reaction.

The stable free radical agent moderated polymerization reactions may be performed in a variety of media, for example suspension, emulsion, bulk, that is neat or without solvent, or in aqueous or nonaqueous solution, using preferably higher boiling solvents such as toluene and xylene.

During the reaction of monomer or mixed monomers to form polymers, the accelerated reaction time may be varied over an effective period of from about 1 to about 10 hours, preferably between about 2 to 5 hours and optimally about 4 hours. The optimal reaction time may vary depending upon the temperature, the volume and scale of the reaction, and the quantity and type of polymerization initiator and stable free radical agent selected.

The polymerization reaction temperature is retained relatively constant throughout the heating step by providing an adjustable external heat source and this temperature is from about 95° C. to about 165° C. (Centigrade), and preferably between 120° C. and 160° C., and optimally in embodiments about 120° C. to 140° C. Reactions performed above 165° C. tend to result in a broadening of the polydispersity. A reaction volume may be selected for any size that enables simple adding, mixing, reacting and isolating the product resins on an economic or convenient scale. The molar ratio of the stable free radical (SFR) agent to free radical initiator (INIT) is from about 0.4 to about 2.5, or the range of from about 0.9 to about 1.6, or the molar ratio [SFR:INIT] of stable free radical agent, for example TEMPO, to free radical initiator, for example benzoyl peroxide, of about 1.3 is believed to be important for success of the process. The molar ratio of monomer content to stable free radical agent to free radical initiator is, for example, from about 100:0.2:1 to about 10,000:2.5:1 and preferably in the range of about 300:1.3:1 to about 7,000:1.3:1.

The stable free radical polymerization processes of the present invention, in embodiments, provide for high monomer to polymer conversion rates, or degrees of polymerization, for example of 90 percent by weight or greater, and more specifically, from about 90 to about 99 percent. Also, the processes of the present invention, in embodiments, provide for relatively high weight average molecular weights, from weight average molecular weights ranging from about 10,000 to about 500,000, or greater in embodiments. The monomers that can be selected include substantially any monomer capable of undergoing a free radical polymerization and include but are not limited to styrene, substituted styrenes and derivatives thereof, for example methylstyrene, acrylates, methacrylates, butadiene and any conjugated diene monomer sufficiently reactive under the specified stable free radical moderated polymerization reaction conditions to afford a stable free radical reaction adduct and high molecular weight polymer product, for example isoprene and myrcene. Specific monomers include styrene, butylacrylate, butylmethacrylate, butadiene, acrylonitrile, chloromethylstyrene, and other known monomers.

By cooling the polymerization reaction to below 60° to 80° C., the stable free radical moderated reaction is effectively quenched or terminated. Each new or subsequent addition of monomer, stable free radical, transition metal, and initiator accompanied by heating provides a new polymeric species having a narrow molecular weight distribution, and each new polymer species continues to grow independent of the other polymer species already established.

Alternatively, block copolymer resins may also be prepared whereby after each desired block has been formed a new monomer or monomers is added without the addition of more initiator, transition metal, or stable free radical agent to form a new block wherein each block component is well defined in length and has a narrow molecular weight distribution, and having properties depending on the repeated sequence and the monomers chosen for incorporation.

Additional optional known additives may be used in the polymerization reactions which do not interfere with the objects of the invention and which may provide additional performance enhancements to the resulting product, for example colorants, lubricants, release or transfer agents, surfactants, stabilizers, antifoams, and the like.

The processes of the present invention can be selected to form a wide variety of polymers. For example, the processes can be selected to polymerize a styrene monomer to form polystyrene, butadiene to form polybutadiene, or acrylate to form an acrylate containing polymer. The process of the present invention can be selected to polymerize a mixture of two or more different polymerizable monomers to form copolymers therefrom, for example polymerization of styrene and butadiene to form poly(styrene-butadiene), styrene and isoprene to form poly(styrene-isoprene), styrene and acrylate to form poly(styrene-acrylate), styrene and methyl methacrylate to form poly(styrene-methyl methacrylate), and the like, and combinations thereof, including copolymers and terpolymers.

There can be incorporated into the monomer a waxy component, such as alkylenes, like polyethylene, polypropylene waxes, and mixtures thereof having a low molecular weight of from between about 1,000 to about 20,000. The use of such a component may be desirable for certain toner applications. Suitable low molecular weight waxes are disclosed in U.S. Pat. No. 4,659,641, the disclosure of which is totally incorporated herein by reference.

Toner compositions can be prepared with the polymer obtained by a number of known methods, such as admixing and heating thermoplastic resin or polymer particles obtained with the processes of the present invention such as styrene acrylate styrene methacrylate, or styrene butadiene copolymers, pigment particles such as magnetite, carbon black, or mixtures thereof, and cyan, yellow, magenta, green, brown, red, or mixtures thereof, and preferably from about 0.5 percent to about 5 percent of charge enhancing additives in a toner extrusion device, such as the ZSK53 available from Werner Pfleiderer, and removing the formed toner composition from the device. Subsequent to cooling, the toner composition is subjected to grinding utilizing, for example, a Sturtevant micronizer for the purpose of achieving toner particles with a volume median diameter of less than about 25 microns, and preferably of from about 6 to about 12 microns, which diameters are determined by a Coulter Counter. Subsequently, the toner compositions can be classified utilizing, for example, a Donaldson Model B classifier for the purpose of removing toner fines, that is toner particles less than about 4 microns volume median diameter.

Illustrative examples of suitable thermoplastic toner resins selected for the toner and developer compositions include polyamides, styrene acrylates, styrene methacrylates, styrene butadienes, vinyl resins, including homopolymers and copolymers of two or more vinyl monomers; vinyl monomers include styrene, p-chlorostyrene, butadiene, isoprene, and myrcene; vinyl esters like esters of monocarboxylic acids including methyl acrylate, ethyl acrylate, n-butyl acrylate, isobutyl acrylate, dodecyl acrylate, n-octyl acrylate, phenyl acrylate, methyl methacrylate, ethyl methacrylate, and butyl methacrylate; acrylonitrile, methacrylonitrile, acrylamide; and the like, including other known thermoplastic toner resins. Preferred toner resins can include styrene butadiene copolymers, mixtures thereof, and the like. Preferred toner resins include styrene/methacrylate copolymers, PLIOLITES®; suspension polymerized styrene butadienes, reference U.S. Pat. No.

4,558,108, the disclosure of which is totally incorporated herein by reference.

In the toner compositions, the resin particles are present in a sufficient but effective amount, for example from about 70 to about 90 weight percent. Thus, when 1 percent by weight of the charge enhancing additive is present, and 10 percent by weight of pigment or colorant, such as carbon black, is contained therein, about 89 percent by weight of resin is selected. Also, the charge enhancing additive may be coated on the pigment particle. When used as a coating, the charge enhancing additive is present in an amount of from about 0.1 weight percent to about 5 weight percent, and preferably from about 0.3 weight percent to about 1 weight percent.

Numerous well known suitable toner pigments or dyes can be selected as the colorant for the toner including, for example, carbon black like REGAL 330®, nigrosine dye, aniline blue, cyan, magenta, yellow, red, green, magnetite, or mixtures thereof. The pigment, which is preferably carbon black, is usually present in a sufficient amount to render the toner composition highly colored. Generally, the pigment is present in amounts of from about 1 percent by weight to about 20 percent by weight, and preferably from about 2 to about 10 weight percent based on the total weight of the toner composition; however, lesser or greater amounts of pigment may be selected.

When the pigment particles are comprised of magnetites, thereby enabling single component toners in some instances, which magnetites are a mixture of iron oxides ($FeO \cdot Fe_2O_3$) including those commercially available as MAPICO BLACK®, they are present in the toner composition in an amount of from about 10 percent by weight to about 70 percent by weight, and preferably in an amount of from about 10 percent by weight to about 50 percent by weight. Mixtures of carbon black and magnetite with from about 1 to about 15 weight percent of carbon black, and preferably from about 2 to about 6 weight percent of carbon black, and magnetite, such as MAPICO BLACK®, in an amount of, for example, from about 5 to about 60, and preferably from about 10 to about 50 weight percent can be selected.

There can also be blended with the toner compositions external additive particles including flow aid additives, which additives are usually present on the surface thereof. Examples of these additives include colloidal silicas, especially fumed silicas, such as AEROSIL®, metal salts and metal salts of fatty acids inclusive of zinc stearate, aluminum oxides, titanium oxides, cerium oxides, and mixtures thereof, which additives can be present in an amount of from about 0.1 percent by weight to about 5 percent by weight, and preferably in an amount of from about 0.1 percent by weight to about 1 percent by weight. Several of the aforementioned additives are illustrated in U.S. Pat. Nos. 3,590,000 and 3,800,588, the disclosures of which are totally incorporated herein by reference.

The colloidal silicas, such as AEROSIL®, can be surface treated with the charge additives in an amount of from about 1 to about 30 weight percent and preferably 10 weight percent followed, by the addition thereof to the toner in an amount of from about 0.1 to 10 and preferably 0.1 to 1 weight percent.

Also, there can be included in the toner compositions low molecular weight waxes, such as polypropylenes and polyethylenes commercially available from Allied Chemical and Petrolite Corporation, EPOLENE N-15® commercially available from Eastman Chemical Products, Inc., VISCOL 550-P®), a low weight average molecular weight polypropylene available from Sanyo Kasei K.K., and similar materials. The commercially available polyethylenes selected have a molecular weight, $M_w$, of from about 1,000 to about 1,500, while the commercially available polypropylenes utilized for the toner compositions are believed to have a molecular weight, $M_w$, of from about 4,000 to about 10,000. Many of the polyethylene and polypropylene compositions are illustrated in British Patent No. 1,442,835, the disclosure of which is totally incorporated herein by reference.

The low molecular weight wax is present in the toner composition or the polymer resin in various amounts, however, generally these waxes are present in the toner composition in an amount of from about 1 percent by weight to about 15 percent by weight, and preferably in an amount of from about 2 percent by weight to about 10 percent by weight, and may in embodiments function as fuser roll release agents.

For the formulation of developer compositions, there are mixed with the toner particles carrier components, particularly those that are capable of triboelectrically assuming an opposite polarity to that of the toner composition. Accordingly, the carrier particles are selected to be of a negative polarity enabling the toner particles, which are positively charged, to adhere to and surround the carrier particles. Illustrative examples of carrier particles include iron powder, steel, nickel, iron, ferrites, including copper zinc ferrites, and the like. Additionally, there can be selected as carrier particles nickel berry carriers as illustrated in U.S. Pat. No. 3,847,604, the disclosure of which is totally incorporated herein by reference. The selected carrier particles can be used with or without a coating, the coating generally containing terpolymers of styrene, methylmethacrylate, and a silane, such as triethoxy silane, reference U.S. Pat. No. 3,526,533, U.S. Pat. No. 4,937,166, and U.S. Pat. No. 4,935,326, the disclosures of which are totally incorporated herein by reference, including, for example, KYNAR® and polymethylmethacrylate mixtures (40/60). Coating weights can vary as indicated herein; generally, however, from about 0.3 to about 2, and preferably from about 0.5 to about 1.5 weight percent coating weight is selected.

Furthermore, the diameter of the carrier particles, preferably spherical in shape, is generally from about 50 microns to about 1,000 microns, and in embodiments from about 90 to about 175 microns thereby permitting them to possess sufficient density and inertia to avoid adherence to the electrostatic images during the development process. The carrier component can be mixed with the toner composition in various suitable combinations, for example about 1 to 5 parts per toner to about 10 parts to about 200 parts by weight of carrier are selected.

The toner and developer compositions may be selected for use in electrostatographic imaging apparatuses containing therein conventional photoreceptors providing that they are capable of being charged positively or negatively. Thus, the toner and developer compositions can be used with layered photoreceptors that are capable of being charged negatively, such as those described in U.S. Pat. No. 4,265,990, the disclosure of which is totally incorporated herein by reference. Illustrative examples of inorganic photoreceptors that may be selected for imaging and printing processes include selenium; selenium alloys, such as selenium arsenic, selenium tellurium and the like; halogen doped selenium substances; and halogen doped selenium alloys.

Embodiments of the present invention include a process for the preparation of 4-oxo-2,2,6,6-tetramethyl-1-piperidinyloxy, which comprises the reaction of triacetone amine in the presence of a catalyst and a peroxide; a process for the preparation of 4-oxo-2,2,6,6-tetramethyl-1-piperidinyloxy, which comprises the reaction of a triacetone amine, a bases, such as ethylenediaminetetraacetic acid, or the salts thereof, and a peroxide in the presence of a catalyst, water, and an aliphatic alcohol; a process wherein the alcohol contains from 1 to about 25 carbon atoms; a process wherein the alcohol is methanol; a process wherein the catalyst is an alkali metal tungstate; a process wherein the catalyst is sodium tungstate dihydrate; a process wherein the peroxide is hydrogen peroxide; a process wherein the catalyst is sodium tungstate dihydrate, the peroxide is hydrogen peroxide, the alcohol is methanol, and the bases is ethylenediaminetetraacetic acid tetrasodium salt; a process wherein the reaction is accomplished at a temperature of from about 25° to about 50° C.; a process wherein the reaction is accomplished at a temperature of from about 25° to about 45° C.; a process wherein the reaction is accomplished at a temperature of from about 30° to about 40° C.; a process wherein the temperature is from about 25° to about 45° C., the catalyst is selected in an amount of from about 1 to about 5 parts, the peroxide is selected in an amount of from about 100 to about 400 parts, the EDTA is selected in an amount of from about 5 to about 20 parts, water is selected in an amount of from about 250 to about 1,000 parts, and the alcohol is selected in an amount of from about 250 to about 1,000 parts; a process wherein the reaction time is from about 5 hours to about 24 hours, the yield of product is from about 35 to about 80 percent, and the product purity is from about 95 to about 99 percent; a process wherein the reaction time is rapid, for example from about 5 hours to about 24 hours, or from about 5 hours to about 10 hours; a process wherein there is selected a temperature of from about 25° to about 45° C., the catalyst is sodium tungstate selected in an amount of from about 1 to about 5 grams, the peroxide is hydrogen peroxide selected in an amount of from about 100 to about 400 grams, the salt is ethylenediaminetetraacetic acid trasodium salt, water is selected in an amount of from about 250 to about 1,000 grams, the alcohol is methanol selected in an amount of from about 250 to about 1,000 grams; a process for the preparation of 4-oxo-2,2,6,6-tetramethyl-1-piperidinyloxy which comprises the catalytic oxidation of triacetone amine; a process wherein the preparation is accomplished in the presence of a peroxide and an alkyl alcohol with heating; a process wherein the catalyst is an alkali metal tungstate; and a process wherein the catalyst is sodium tungstate dihydrate, and the peroxide is hydrogen peroxide. Amounts not specifically recited herein may be selected in embodiments of the present invention.

The following Examples are provided. Parts and percentages are by weight unless otherwise indicated. Comparative Examples and data are also provided.

COMPARATIVE EXAMPLE

A solution of 155 grams of triacetone amine, 15 grams of TRILON B™ (N,N-1,2-ethanediylbis[N-carboxymethyl] glycine] tetrasodium salt, available from Aldrich Chemicals), and 15 grams of sodium tungstate in 1,000 milliliters of water was cooled to 3° C. to 5° C. and 250 milliliters of 30 percent hydrogen peroxide were added, after which, by external cooling, the temperature within the reaction flask was retained between 15° C. and 18° C. for 4 to 6 hours. Subsequently, the reaction mixture was retained in the dark at room temperature, about 25° C., for 8 to 10 days. The resulting reddish-yellow solution was saturated with potassium carbonate. The radical, which had separated in the form of a dark red oil, crystallized on cooling to about 25° C. It was filtered off with suction, pressed out on the filter paper, and dried in a vacuum desiccator over potassium hydroxide. Yield was 160 to 170 grams. After recrystallization from a minimum amount of hexane, 130 to 140 grams of TEMPONE, an abbreviation for 2,2,6,6-tetramethyl-4-oxopiperidine-1-oxyl, was obtained in the form of pink needles, melting point 36° C. The oxime, isolated as red crystals from methanol, had a melting point of 180° C. (Centigrade throughout).

The above slow reaction time of 7 to 10 total days is not considered scaleable, especially for semicommercial, or commercial purposes.

EXAMPLE I

Catalytic Oxidation of Triacetone Amine (TAA) to 4-Oxo-TEMPO

There were charged, or added to a 1 liter glass jacketed reactor equipped with a stirrer, a resistance temperature detector (RTD), a water condenser, and a dropping funnel 68 grams of triacetone amine, 2.32 grams of sodium tungstate dihydrate, 119.9 grams of hydrogen peroxide (30 percent), 7.7 grams of ethylenediaminetetraacetic acid (EDTA) tetrasodium salt, 250 grams of water, and 250 grams of the aliphatic alcohol methanol. The TAA was recrystallized from n-heptane before use. The reactor jacket temperature was adjusted to 33° C. At this temperature, the 30 percent aqueous $H_2O_2$ solution was added dropwise over 30 minutes. The reaction mixture was then stirred for another 7.5 hours at 33° C.

The EDTA primarily acts like a base, however, the EDTA has the added advantage in that it complexes with heavy metal ions which are known to decompose hydrogen peroxide, and thus the EDTA is believed to contribute to the stability of hydrogen peroxide.

The resulting reaction mixture was extracted with two portions of 200 grams of methylene chloride and the extracts combined in a round bottom flask. The solvent methylene chloride was evaporated under vacuum down to 125 grams of the extract solution. The extract solution was topped with 450 grams of heptane and retained in a freezer at −25° C. over night, about 18 hours. The 4-oxo-TEMPO product, that is 4-oxo-2,2,6,6-tetramethyl-1-piperidinyloxy product, recrystallized from the heptane/methylene chloride solution, and was filtered on cold heptane and washed with heptane to provide an isolated yield of 25.3 grams. The retenate was dried under a nitrogen stream until a constant weight of 5.1 grams was obtained. Total product recovered was 30.4 grams or 40.8 percent of theoretical yield. The melting point was found to be from 38° C. to 39° C., according to a DSC measurement. A single, sharp peak in the DSC indicated a high purity, from 95 to 99 percent pure, of the thus recovered 4-oxo-TEMPO product.

The progress of the above catalytic sodium tungstate dihydrate oxidation reaction of TAA to 4-oxo-TEMPO was followed by the UV spectroscopy in a 0.01 percent solution of water/methanol (50/50 w/w). The ratio of the absorbances of two characteristic peaks (the first one at 200 to 202 nanometers, and the second at 224 to 236 nanometers), indicates the progress of the reaction.

The above Example reaction can be repeated with, for example, the following parameters:

Temperature: 25° to 45° C.;

Sodium Tungstate: 1 to 5 grams;

100 to 400 grams of hydrogen peroxide (30 percent);

5 to 20 grams of EDTA, tetrasodium salt (other bases such as sodium bicarbonate or sodium acetate may, it is believed, be substituted for EDTA);

250 to 1,000 grams of water;

250 to 1,000 grams of methanol;

Addition time: 30 minutes to 3 hours;

Reaction time: 5 to 24 hours; and

Yield Ranges: 35 to 80 percent.

The product was identified by melting point, electron spin resonance, UV-Visible Spectroscopy and Infrared.

Full Chemical Name for TEMPONE (or 4-oxo-TEMPO) is 4-oxo-2,2,6,6-tetramethyl-1 -piperidinyloxy.

EXAMPLE II

Triacetone amine (6.8 grams), sodium tungstate dihydrate (232 milligrams) and ethylenediaminetetraacetic acid disodium salt (773 milligrams) were dissolved in 25 milliliters of water and 25 milliliters of ethanol in a 250 milliliter Erlenmeyer flask. The reaction mixture was heated to 32° C. and 10.8 milliliters of 35 percent by weight aqueous hydrogen peroxide were added dropwise over 30 minutes. At this reaction temperature very little exotherm was noticed but the color of the solution lightened perceptibly and some gas evolution was evident. After 5 hours, the reaction was cooled and extracted with methylene chloride (2 portions of 30 milliliters each). After evaporation of the methylene chloride, the TEMPONE was sublimed to yield 4.31 grams (58 percent of the theoretical yield) of an orange solid, TEMPONE which had a purity of 103, 99±4 percent as determined by electron spin resonance.

Other embodiments and modifications of the present invention may occur to those skilled in the art subsequent to a review of the information presented herein; these embodiments and modifications, as well as equivalents thereof, are also included within the scope of this invention.

What is claimed is:

1. A process for the preparation of 4-oxo-2,2,6,6-tetramethyl-1-piperidinyloxy which comprises the reaction of triacetone amine in the presence of a catalyst and a peroxide, and wherein said reaction time is from about 3 to about 7 hours.

2. A process in accordance with claim 1 wherein the reaction is accomplished in the presence of a base.

3. A process in accordance with claim 2 wherein the base is ethylenediaminetetraacetic acid (EDTA).

4. A process for the preparation of 4-oxo-2,2,6,6-tetramethyl-1-piperidinyloxy, which comprises the reaction of a triacetone amine, a base, and a peroxide, in the presence of a catalyst, water, and an aliphatic alcohol, and wherein said reaction time is from about 3 to about 7 hours.

5. A process in accordance with claim 4 wherein the base is ethylenediaminetetraacetic acid.

6. A process in accordance with claim 4 wherein the alcohol contains from 1 to about 25 carbon atoms.

7. A process in accordance with claim 4 wherein the alcohol is methanol.

8. A process in accordance with claim 7 wherein the catalyst is sodium tungstate dihydrate.

9. A process in accordance with claim 4 wherein the peroxide is hydrogen peroxide.

10. A process in accordance with claim 4 wherein the catalyst is sodium tungstate dihydrate, the peroxide is hydrogen peroxide, the alcohol is methanol, and the base is ethylenediaminetetraacetic acid, or a tetra alkali salt thereof.

11. A process in accordance with claim 10 wherein the salt is ethylenediaminetetraacetic acid tetrasodium salt.

12. A process in accordance with claim 4 wherein the reaction is accomplished at a temperature of from about 25° C. to about 50° C.

13. A process in accordance with claim 4 wherein the reaction is accomplished at a temperature of from about 25° C. to about 45° C.

14. A process in accordance with claim 5 wherein the reaction is accomplished at a temperature of from about 25° C. to about 45° C.

15. A process in accordance with claim 4 wherein the reaction is accomplished at temperature of from about 25° C. to about 45° C., the catalyst is selected in an amount of from about 1 to about 5 parts, the peroxide is selected in an amount of from about 100 to about 400 parts, the EDTA is selected in an amount of from about 5 to about 20 parts, water is selected in an amount of from about 250 to about 1,000 parts, and the alcohol is selected in an amount of from about 250 to about 1,000 parts.

16. A process in accordance with claim 4 wherein the reaction time is from about 3 hours to about 4.5 hours, the yield of product is from about 35 to about 80 percent, and the product purity is from about 95 to about 99 percent.

17. A process in accordance with claim 4 wherein the reaction time is from about 3 hours to about 4.5 hours.

18. A process in accordance with claim 4 wherein there is selected a temperature of from about 25° C. to about 45° C., the catalyst is sodium tungstate selected in an amount of from about 1 to about 5 grams, the peroxide is hydrogen peroxide selected in an amount of from about 100 to about 400 grams, the base is ethylenediaminetetraacetic acid tetrasodium salt, water is selected in an amount of from about 250 to about 1,000 grams, and the alcohol is methanol selected in an amount of from about 250 to about 1,000 grams.

19. A process in accordance with claim 1 wherein the reaction time is 7.5 hours and the reaction is accomplished by heating at a temperature of 33° C.; or wherein the reaction time is 5 hours and the reaction is accomplished by heating at a temperature of 32° C.

20. A process for the preparation of 4-oxo-2,2,6,6-tetramethyl-1-piperidinyloxy which comprises the reaction of a triacetone amine in the presence of a catalyst, a peroxide, and an aliphatic alcohol, and which reaction is accomplished in a period of from about 3 to about 7 hours at a temperature of from about 25° C. to about 45° C.

21. A process in accordance with claim 20 wherein the reaction time is from about 3 to about 4.5 hours.

22. A process for the preparation of 4-oxo-2,2,6,6-tetramethyl-1-piperidinyloxy which consists essentially of the reaction of a triacetone amine in the presence of a catalyst, a peroxide, and an aliphatic alcohol, and which reaction is accomplished in a period of from about 3 to about 7 hours at a temperature of from about 25° C. to about 45° C.

23. A stable free radical polymerization process for the preparation of polymers which comprises heating a mixture of a free radical initiator, a stable free radical agent, and at least one polymerizable monomer such that all polymer change formations are initiated at about the same time, and wherein there is selected as the stable free radical agent 4-oxo-2,2,6,6-tetramethyl-1-piperidinyloxy, and wherein said stable free radical agent is prepared by the reaction of triacetone amine, a base, and a peroxide in the presence of a catalyst and an aliphatic alcohol, and wherein said reaction time is from about 3 to about 7 hours.

* * * * *